US011793461B2

(12) United States Patent
Gad et al.

(10) Patent No.: US 11,793,461 B2
(45) Date of Patent: Oct. 24, 2023

(54) FOOTBALL SMART FOOTWEAR WITH AUTOMATIC PERSONAL AND TEAM PERFORMANCE STATISTICS EXTRACTION

(71) Applicant: MOTIONIZE ISRAEL LTD., Tel Aviv (IL)

(72) Inventors: Moran Gad, Nahal Oz (IL); Asaf Erez, Nes Ziona (IL); Guy Aharon, Hertzliya (IL); Gil Lemel, Hertzliya (IL); Nir Levi, Jerusalem (IL); Sivan Postelnik, SE Marietta, GA (US); Yuval Odem, Hadera (IL); Eyal Postelnik, SE Marietta, GA (US); Erez Morag, Caesarea (IL)

(73) Assignee: MOTIONIZE ISRAEL LTD., Tel Aviv (IL)

( * ) Notice: Subject to any disclaimer, the term of this patent is extended or adjusted under 35 U.S.C. 154(b) by 723 days.

(21) Appl. No.: 16/492,139

(22) PCT Filed: Mar. 7, 2018

(86) PCT No.: PCT/IL2018/050264
§ 371 (c)(1),
(2) Date: Sep. 8, 2019

(87) PCT Pub. No.: WO2018/163175
PCT Pub. Date: Sep. 13, 2018

(65) Prior Publication Data
US 2020/0229762 A1     Jul. 23, 2020

Related U.S. Application Data

(60) Provisional application No. 62/467,838, filed on Mar. 7, 2017.

(51) Int. Cl.
*A61B 5/00* (2006.01)
*A43B 5/02* (2006.01)
(Continued)

(52) U.S. Cl.
CPC .............. *A61B 5/6831* (2013.01); *A43B 3/34* (2022.01); *A43B 5/02* (2013.01); *A43C 19/00* (2013.01);
(Continued)

(58) Field of Classification Search
CPC ... A61B 5/6831; A61B 5/1123; A61B 5/6807; A61B 2503/10; A43B 5/02; A43B 3/34; A43C 19/00
(Continued)

(56) References Cited

U.S. PATENT DOCUMENTS

| 6,112,961 A | 9/2000 | Phillips |
| 2004/0082414 A1 | 4/2004 | Knox |

(Continued)

FOREIGN PATENT DOCUMENTS

| CA | 2883098 | * | 6/2012 |
| CN | 201790034 U | | 4/2011 |

(Continued)

OTHER PUBLICATIONS

Nguyen et al., (2015) Dynamic Human Gait Phase Detection Algorithm. The ISSAT International Conference on Modeling of Complex Systems and Environments (MCSE) Jun. 8-10, 2015, Da Nang, Vietnam. 5 pages.
(Continued)

*Primary Examiner* — Robert R Raevis
(74) *Attorney, Agent, or Firm* — The Roy Gross Law Firm, LLC; Roy Gross

(57) ABSTRACT

A system, method and footwear sensor unit a footwear sensor unit removably attachable to footwear, the footwear sensor unit including: an Inertial Measurement Unit (IMU) including a 3-axis accelerometer and a 3-axis gyroscope, the IMU adapted to gather sensor data of detected movements of the footwear; and a storage device in electronic communi-
(Continued)

cation with the IMU, the storage device for storing the sensor data; and a communications module in electronic communication with the storage device, the communication module configured to transmit data to an external computing device.

10 Claims, 11 Drawing Sheets

(51) Int. Cl.
| | |
|---|---|
| A43C 19/00 | (2006.01) |
| A61B 5/11 | (2006.01) |
| A43B 3/34 | (2022.01) |

(52) U.S. Cl.
CPC .......... *A61B 5/1123* (2013.01); *A61B 5/6807* (2013.01); *A61B 2503/10* (2013.01)

(58) Field of Classification Search
USPC .................. 702/33, 142, 149, 150, 151, 179; 73/862.01, 1.75, 1.77, 1.37, 1.38, 493, 73/503, 503.3, 504.02–504.16, 73/514.01–514.38
See application file for complete search history.

(56) References Cited

U.S. PATENT DOCUMENTS

| | | |
|---|---|---|
| 2006/0261107 A1 | 11/2006 | Daniels |
| 2008/0018066 A1 | 1/2008 | Pickford |
| 2008/0185799 A1 | 8/2008 | Weisiger |
| 2008/0249736 A1* | 10/2008 | Prstojevich ............ A63B 24/00 702/141 |
| 2010/0184563 A1 | 7/2010 | Molyneux |
| 2010/0305480 A1 | 12/2010 | Fu et al. |
| 2011/0054359 A1 | 3/2011 | Sazonov |
| 2011/0066383 A1 | 3/2011 | Jangle et al. |
| 2013/0123665 A1 | 5/2013 | Mariani et al. |
| 2013/0244211 A1 | 9/2013 | Dowling et al. |
| 2015/0352419 A1 | 12/2015 | Pappas et al. |
| 2015/0359457 A1 | 12/2015 | Blumenthal |
| 2016/0018278 A1* | 1/2016 | Jeter, II ................. G16H 40/63 340/665 |
| 2016/0262687 A1 | 9/2016 | Vaidyanathan et al. |
| 2016/0309834 A1 | 10/2016 | Zwick et al. |
| 2016/0324445 A1* | 11/2016 | Kim ..................... A61B 5/1038 |

FOREIGN PATENT DOCUMENTS

| | | | |
|---|---|---|---|
| CN | 103442607 A | | 12/2013 |
| CN | 105229664 A | | 1/2016 |
| CN | 105453090 A | | 3/2016 |
| CZ | 30029 | * | 11/2016 |
| EP | 3086320 A1 | | 10/2016 |
| EP | 3092913 A1 | | 11/2016 |
| EP | 3104290 A1 | | 12/2016 |
| TW | 201515636 A | | 5/2015 |
| WO | 03000355 A1 | | 1/2003 |
| WO | 2008010618 A1 | | 1/2008 |
| WO | 2014066779 A2 | | 5/2014 |
| WO | 2015164944 A1 | | 11/2015 |
| WO | 2015197769 | * | 12/2015 |
| WO | 2016037879 A1 | | 3/2016 |

OTHER PUBLICATIONS

CC2640 SimpleLink™ Bluetooth® Wireless MCU. Dated Feb. 2015; revised Jul. 2016. Texas Instruments. Retrieved from: https://www.ti.com/lit/ds/symlink/cc2640.pdf?ts=1601447802402&ref_url=https%253A%252F%252Fwww.ti.com%252Fproduct%252FCC2640, 64 pages.

MPU-9150™; Product Specification. Release Date: Sep. 18, 2013 (Sep. 18, 2013). InvenSense Inc. Sunnyvale, CA, USA. Retrieved from: https://invensense.tdk.com/wp-content/uploads/2015/02/MPU-9150-Datasheet.pdf, 50 pages.

MS5611-01BA03; Barometric Pressure Sensor, with stainless steel cap. Dated Jun. 2017 (Jun. 2017). Measurement Specialties, Inc., a TE Connectivity company. Retrieved from: https://www.te.com/commerce/DocumentDelivery/DDEController?Action=showdoc&DocId=Data+Sheet%7FMS5611-01BA03%7FB3%7Fpdf%7FEnglish%7FENG_DS_MS5611-01BA03_B3.pdf%7FCAT-BLPS0036, 22 pages.

STM32F411CEY6TR (STM32F411xC STM32F411xE) Arm® Cortex®—M4 32b MCU+FPU, 125 DMIPS, 512KB Flash, 128KB RAM, USB OTG FS, 11 TIMs, 1 ADC, 13 comm. Interfaces. Dated Dec. 2017. STMicroelectronics. Retrieved from: https://www.st.com/resource/en/datasheet/stm32f411ce.pdf, 149 pages.

Clark et al., (2017) A general relationship links gait mechanics and running ground reaction forces. Journal of Experimental Biology 220: 247-258 with supplementary information.

PCT Preliminary Report on Patentability for International Application No. PCT/IL2018/050264, dated Sep. 10, 2019, 6 pp.

PCT Search Report for International Application No. PCT/IL2018/050264, dated May 22, 2018, 3 pp.

PCT Written Opinion for International Application No. PCT/IL2018/050264, dated May 22, 2018, 5 pp.

Bamberg et al., (2008) Gait Analysis Using a Shoe-Integrated Wireless Sensor System. IEEE Transactions on Information Technology in Biomedicine 12(4): 413-423.

* cited by examiner

FIG. 9 – Table 1

| Topic | Motivation | Parameters | Description | System blocks in use |
|---|---|---|---|---|
| Touch count | -Quantify player involvement coaching wise and performance wise<br>-Quantify player control in both legs<br>-Identify weakness in player ball control | Total Touch Count | the sum of ball touches of a single player in a training session and/or a drill. | (1) Touch classifier (for each foot/sensor);<br>(2) touch type classifier;<br>(3) sensor data fusion – post process touch type algorithm |
| | | Leg Use | Total ball touch of each leg divided to total touch | |
| | | Touch Type Distribution | the sum of ball touches per type (receive, release, dribbling) | |
| Ball Possession (BP) | -Quantify player playing tempo coaching wise and performance wise<br>-Tactical analysis of team playing tempo in coordinating to coach objectives | Individual BP (IBP) total count | IBP count | (1) Touch classifier (for each foot/sensor);<br>(2) touch type classifier;<br>(3) Gait Tracking algorithm;<br>(4) sensor data fusion – post process IBP algorithm |
| | | individual BP type count | Types of IBP counter:<br># Multiple IBP <X sec<br># Multiple IBP >X sec<br># 1 touch | |
| | | BP time distribution (player/team) | Different players statistics regarding the BP time | |
| | | Team BP (TBP) time [%] | sum of TBP time of each team divided by total TBP time of both teams | |
| Passes, Retrieves and Possession lost | -Quantify player accuracy<br>-Quantify the player attacking contribution<br>-Quantify player defensive contribution<br>-Quantify player decision making<br>-Quantify player reaction after event<br>-Attacking build up analysis in coordinating to coach objectives | Total pass count (player/team) | Total pass count (player/team) | (1) sensor data fusion – post process IBP algorithm;<br>(2) sensor data fusion – post process sequence algorithm |
| | | Successful pass [%] (player/team) | % of successful passes out of player/team total # of passes | |
| | | Passing network | The distributions of a team's/player's successful passes | |
| | | Passes per team possession | # of completed passes per TBP | |
| | | Retrieve count | Retrieve count | |
| | | Retrieve effort (did he sprint after team lost possession) | % of positive reaction by player after lost possession | |
| | | Possession lost count | Possession lost count | |
| | | Retrieve time (player/team average) | Retrieve time (player/team average) | |

FIG. 9 – Table 1 cont.

| Physical | -Monitor workload -Predict injuries -Prevent injuries -Quantify player physical performance | Total distance | Total session distance of each player | (1) Gait Tracking algorithm; (2) sensor data fusion – post process gait tracking algorithm |
| --- | --- | --- | --- | --- |
| | | Distance per drill | Total session distance of each player per drill | |
| | | Distance per speed zone | Total session distance of each player per speed zone (the speed zones are defined by user input) | |
| | | Max speed | The maximum instant speed of each player. | |
| | | Work rate | Total duration / total distance | |
| | | Sprint count | Count over for each time a player run above velocity X and passed Y meter at this velocity (X and Y are user input variables) | |
| | | Sprint distance | Total distance over velocity X (X is defined by user input) | |
| | | Accel\Dec count by zones | A count for each time a player reached acceleration in the acceleration zones defined by user. | |
| | | Total player's mechanical load | Mechanical load index – quantifies the mechanical load of each player, high values might indicate a load injury risk. | |
| | | Mechanical by leg (dominant/non-dominant) | Mechanical load balance dominant/non-dominant foot. | |

FOOTBALL SMART FOOTWEAR WITH AUTOMATIC PERSONAL AND TEAM PERFORMANCE STATISTICS EXTRACTION

FIELD OF THE INVENTION

The present invention relates to a device, system and method for sensing and extracting performance statistic of soccer players.

BACKGROUND OF THE INVENTION

Performance statistics of individual soccer players as well as those of a team as a whole are key elements in the field of player/team coaching and personal improvement. Coaches and players use the performance statistics to make decisions regarding skills that affect the players' technical and tactical performance. The extraction of the performance statistics, today, comes from two main sources: (1) video tagging (2) GPS based system.

The video tagging is done manually using tagging software and then by simple static-related calculations over the tagged data. Aside from other labels, operators mainly tag ball-touch events (events where the player touches the ball, e.g. dribbling, passing, shooting etc.). The video tagging process is long and expensive. As such, only a few well-funded football clubs can afford the process. Even then, video tagging is mainly used for football matches but not for training.

The GPS based system supplies position-driven data. Therefore, the performance statistics that can be extracted from the GPS based system are generally distance, speed, acceleration and some estimation of the player's mechanical power and load.

SUMMARY OF THE INVENTION

The presently disclosed system replaces the data sources discussed above with a wearable smart-device that is mounted on the shoe. The performance data is sensed, stored and extracted in an automated manner with a high degree of accuracy. The innovative system does requires almost no manual tagging and presents the entire suite of performance statistics that football clubs use today as well as a great deal of data that known systems are unable to provide.

Since the system is fully automated it is accessible to any football club at any level. The system is the first ever complete system for extraction of football performance statistics from individual players and the team as a whole. The present solution includes designated mechanics, hardware, firmware and various kinds of football-centered algorithms.

According to the present invention there is provided a footwear sensor unit removably attachable to footwear, the footwear sensor unit including: an Inertial Measurement Unit (IMU) including a 3-axis accelerometer and a 3-axis gyroscope, the IMU adapted to gather sensor data of detected movements of the footwear; and a storage device in electronic communication with the IMU, the storage device for storing the sensor data; and a communications module in electronic communication with the storage device, the communication module configured to transmit data to an external computing device.

According to further features the sensor unit further includes: a processing unit in electronic communication with the IMU, the storage device and communications module, the processing unit and configured to classify the sensor data into event data indicative of gait tracking data, foot activity events and ball-touch events.

According to further features in preferred embodiments of the invention described below the communication module includes at least one of a physical communications mechanism and a wireless communication mechanism and is adapted to electronically communicate the sensor data or the event data to an external computing device According to still further features in the described preferred embodiments the external computing device is selected from the group including: a second footwear sensor unit, a synchronization station, a computer server and a computing device.

According to further features the footwear sensor unit further includes a data port configured to facilitate data transfer to a synchronization station via a physical connection.

According to further features the footwear sensor unit is housed in, or otherwise operationally coupled to, a mounting strap, the mounting strap adapted to be fitted onto the footwear. According to further features the footwear is selected from the group including: a soccer boot, a shoe, a sneaker. According to further features the footwear sensor unit is positioned at an outside ankle or heel area of the footwear.

According to further features the external computing device processes the sensor data or the event data and returns feedback for a human interface device, the feedback selected from the group including: visual feedback, audio feedback, physical feedback and a combination thereof.

According to another embodiment there is provided a system for providing performance data of participants playing soccer, the system including: at least two footwear sensor units each operationally coupled to a respective footwear; a synchronization station serving as an electronic interface adapted to receive data from the at least two footwear sensor unit; a server computer in electronic communication with the synchronization station, the server computer configured to fuse the received data and output performance parameters.

According to further features the data received at the synchronization station is selected from the group including: raw data and calculated data.

According to further features the raw data includes sensor data selected from the group including: position, acceleration and velocity of each the respective footwear.

According to further features the calculated data includes data calculated by a gait tracking algorithm and a foot-based activity and event detection algorithm, the gait tracking algorithm providing an ability to track orientation and translation of the participants during a gait cycle; and the foot-based activity and event detection algorithm providing an ability to detect different footwear movements and ball interaction events.

According to further features the calculated data is classified in a machine learning process, the machine learning process including an initial stage of receiving a large data set of labeled movement types.

According to further features the server computer is further configured to fuse the received data so as to determine a most likely sequence of hidden states.

According to another embodiment there is provided a method for extracting performance parameters from a footwear sensor unit, the method including: (a) providing the footwear sensor unit on a footwear; (b) receiving, at a processing unit, sensor data from an Inertial Measurement Unit (IMU), the processing unit and IMU being housed in the footwear sensor unit and in electronic communication with one another; and (c) classifying, by the processing unit, a set of the sensor data as event data indicative of a gait event or a foot activity event or a ball touch event.

According to further features the method further comprises (d) communicating the sensor data or the event data to a server computer for extracting performance parameters; and (e) receiving feedback from the server computer, the feedback related to the performance parameters.

According to further features the method the feedback is outputted to a Human Interface Device (HID), and wherein the feedback is selected from the group including: visual feedback, audio feedback, physical feedback and a combination thereof.

According to further features the classifying of the event data indicative of the gait event is performed by employing a gait phase detection algorithm. According to further features the classifying of the event data indicative of the foot activity event or the the ball touch event is performed by employing a foot-based activity and event detection algorithm.

According to further features the performance parameters include one or more of: a Total Touch Count, Leg Use, Touch Type Distribution, ball possession (BP), Individual BP (IBP) total count, individual BP type count, BP time distribution per player and per team, Team BP (TBP) time, Total pass count per player and per team, Successful pass percentage per player and per team, a Passing network, Passes per team possession, a Retrieve count, a Retrieve effort indicative of effort made after team loss of possession, a Possession lost count, an average Retrieve time per player and per team and physical performance parameters.

According to further features the physical performance parameters are selected from the group including: a total distance traversed per player, a distance per drill, a distance per speed zone, a maximum speed, a Work rate, a Sprint count, a Sprint distance, Acceleration and Deceleration count by zones, a total mechanical load per player and a total mechanical load per player.

According to another embodiment there is provided a method for extracting performance parameters, the method including: (a) providing a plurality of footwear sensor units, each of the plurality of footwear sensor units being provided on a respective footwear; (b) receiving sensor data from Inertial Measurement Units (IMU) of the plurality of footwear sensor units in parallel; (c) evaluating the sensor data to receive gait tracking data and event detection data; and (d) fusing the sensor data, the gait tracking data and the event detection data to determine performance statistics and eliminate false detection events.

According to further features the fusing further provides a most likely sequence of hidden states.

According to another embodiment there is provided a mounting system, the system including: a mounting strap including: a back-strap, an upper strap, an under-strap and a holding pouch; and a housing, the housing being removably insertable into the holding pouch of the mounting strap; wherein the mounting strap is adapted to be fitted to on a footwear.

According to further features the mounting strap is made from a material selected from the group including: a flexible material and an elastic material.

According to further features the back-strap is adapted to fit around a heel of the footwear; the under-strap is adapted to be positioned beneath a sole of the footwear; the upper-strap is adapted to lie over an upper of the footwear near a tongue thereof; and the holding pouch is adapted to be positioned on an outside of the footwear, at a heel thereof. According to further features the housing is adapted to hold a footwear sensor unit.

BRIEF DESCRIPTION OF THE DRAWINGS

Various embodiments are herein described, by way of example only, with reference to the accompanying drawings, wherein:

FIG. 9 is a table which details examples of how the above described components of the system are employed to extract various parameters.

DESCRIPTION OF THE PREFERRED EMBODIMENTS

The principles and operation of the smart footwear device and system according to the present invention may be better understood with reference to the drawings and the accompanying description. The terms football and soccer are used interchangeably herein.

Figure 1:
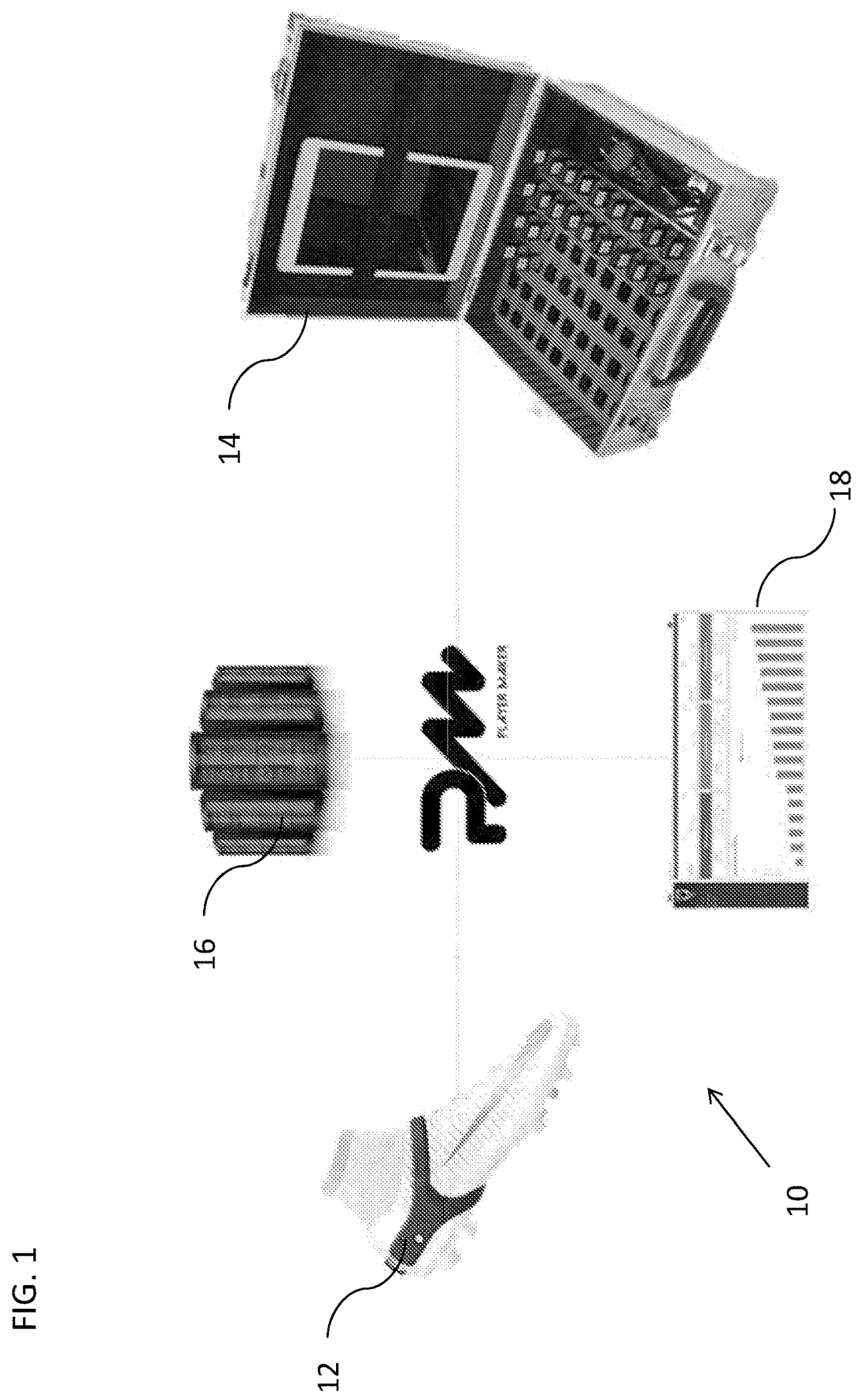
FIG. 1 is a diagram of the components of the system architecture.

FIG. 1 illustrates a diagram including the components of an embodiment of the system architecture. In a preferred embodiment of the system 10 there are four physical elements: (1) a footwear sensor unit 12; (2) a data gateway/synchronizing station 14; (3) servers 16; and (4) a dashboard 18.

In one embodiment, the four units work in a serial manner. The footwear sensor unit 12 includes an Inertial Measurement Unit (IMU) module with, for example, a 6-degrees-of-freedom (6-DOF) motion sensor (as well as other hardware discussed below). The sensor unit 12 is mounted on a player shoe with a unique resilient housing, preferably made from an elastic material, e.g. silicon. The sensor module, housing and mounting strap (which together are referred to herein as the footwear sensor unit 12) are described in greater depth below with reference to FIGS. 2 and 3 respectively. The sensors are active during the game or training session, collecting and analyzing the data from the IMU.

In one embodiment, the synchronizing station 14 contains the hardware which serves as a data collection gateway. In some embodiments, the synchronization station is an electronic interface between the footwear sensor unit and an external computing device (e.g. a local or remote server computer and the like). In embodiments, station 14 is also a charging station for charging the rechargeable batteries of the sensor units. In embodiments a separate charging station is provided for charging the sensor unit. In some embodiments, the footwear sensors worn by the players during practice or games wirelessly transmit the sensor data to the hardware in the synchronizing station 14. In other embodiments, the sensor data is stored in the sensor units until the end of the game/session at which point the sensor units are physically connected to the synchronizing station to download the data. In some of the aforementioned embodiments, the sensor units are charged at the same time. The synchronization station is further configured to synchronize the internal clocks of the footwear sensor units being used in the training session or game.

From the synchronizing station, the data is transmitted/uploaded to the server(s) 16. The data may be uploaded to the server in real-time (or near real-time) or after the game/session for processing, depending on the configuration of the system. The server(s) 16 perform sensor data fusion and prepare the performance statistics for the dashboard. Post-game or post training session data is returned or retrieved from the servers after processing and displayed on a graphic user interface (GUI) dashboard 18. In some embodiments, at least some of the data is processed and displayed on the dashboard prior to the end of the game or training session and/or shortly after the game/session. Users can input queries into the GUI and the servers provide the necessary data which is displayed on the dashboard.

After processing, the external computing device may provide additional or alternative feedback. The feedback may be audio feedback, visual feedback and/or physical feedback (such as haptic feedback, vibration feedback etc.). In some embodiments, the external computing device (e.g. server computer, gateway synchronization station etc.) communicates with a Human Interface Device (HID) to provide the user with audio and/or visual and/or physical (e.g. haptics, vibrations etc.) feedback. Examples of HIDs include, but are not limited to: a display, an ear piece, a haptic/vibration feedback unit (e.g. integrated into the footwear sensor unit or a separate device) or a similar device.

Footwear Sensor Unit Hardware

Various components of the sensor hardware (HW) may be mounted in modules. In preferred embodiments, the modules include one or more of the following: a position sensor; a communication mechanism (for example a module may communicate with another component of the system via a wireless transceiver and/or the module may communicate with a user via a human interface device (HID)); and a power source. In some embodiments, the sensor unit communicates with a HID to provide the user with audio and/or visual and/or physical (e.g. haptics, vibrations etc.) feedback. Examples of HIDs include, but are not limited to: a display, an ear piece, a haptic/vibration feedback unit (e.g. integrated into the footwear sensor unit or a separate device) or a similar device. The sensor unit may further include a processing unit and storage device (memory) for storing the sensor data. The storage device may be integrated one or more of the modules such as the processing unit, IMU, communication module etc.

Figure 2:
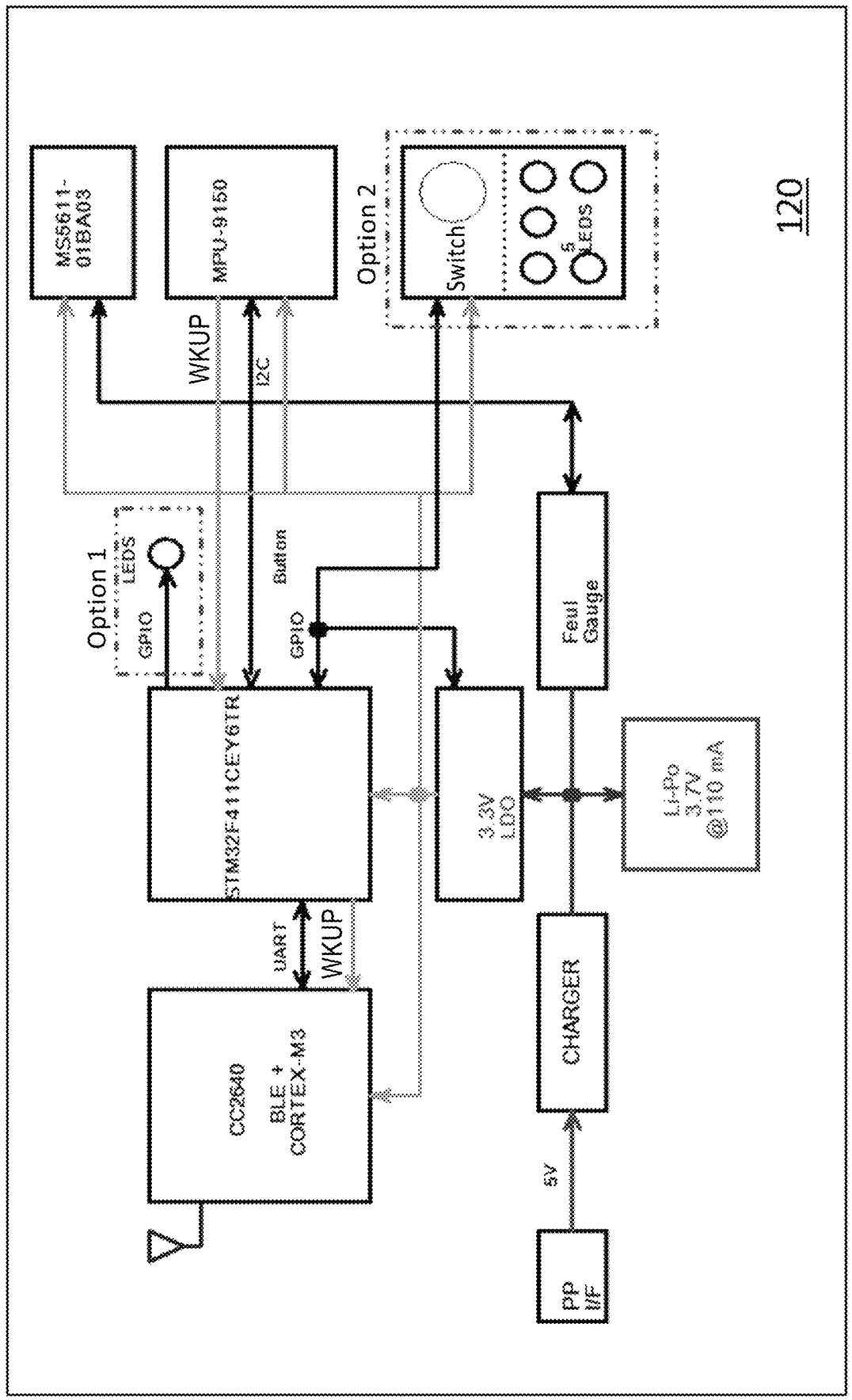
FIG. 2 is a schematic diagram of an exemplary module from the footwear sensor unit.

FIG. 2 illustrates a schematic diagram of an exemplary module from the footwear sensor unit 12. A module 120 includes various hardware components of which only those germane to the innovation will be discussed in detail. Exemplarily, the module 120 includes 6 DOF motion sensor such as an MPU-9150™ made by InvenSense headquartered in San Jose, Calif., USA. The product specification of the MPU-9150™ is incorporated by reference as if fully set forth herein. It is reiterated that the MPU-9150 is merely an exemplary IMU and that any 6 DOF or 9 DOF or other similar motion sensor can be used in place of the aforementioned. In fact, in preferred embodiments, the motion sensor is a 9-DOF motion sensor of which the system only utilizes sensor data from a 3-axis gyroscope and a 3-axis accelerometer, i.e. only 6-DOF. What follows is a listing of features of the MPU-9150. The features are merely exemplary and can be substituted with similar features, or, if not relevant or necessary can be removed outright. The following list is not intended to be limiting in any way whatsoever.

The MPU-9150 is a System in Package (SiP) that combines two chips: the MPU-6050, which contains a 3-axis gyroscope, 3-axis accelerometer, and an onboard Digital Motion Processor™ (DMP™) capable of processing complex MotionFusion algorithms; and the AK8975, a 3-axis digital compass. The integrated 6-axis MotionFusion algorithms access all internal sensors to gather a full set of sensor data.

The triple-axis MEMS gyroscope in the MPU-9150 includes a wide range of features: Digital-output X-, Y-, and Z-Axis angular rate sensors (gyroscopes) with a user-programmable full scale range of ±250, ±500, ±1000, and ±2000°/sec • External sync signal connected to the FSYNC pin supports image, video and GPS synchronization • Integrated 16-bit ADCs enable simultaneous sampling of gyros, and more.

The triple-axis MEMS accelerometer in MPU-9150 includes a wide range of features: Digital-output 3-Axis accelerometer with a programmable full scale range of ±2 g, ±4 g, ±8 g and ±16 g • Integrated 16-bit ADCs enable simultaneous sampling of accelerometers while requiring no external multiplexer • Orientation detection and signaling • Tap detection and more.

The triple-axis MEMS magnetometer in MPU-9150 includes a wide range of features: 3-axis silicon monolithic Hall-effect magnetic sensor with magnetic concentrator • Wide dynamic measurement range and high resolution with lower current consumption. • Output data resolution is 13 bit (0.3 µT per LSB) • Full scale measurement range is ±1200 µT, and more.

The MPU-9150 includes the following exemplary additional features: 9-Axis MotionFusion via on-chip Digital Motion Processor (DMP) • Auxiliary master I2C bus for reading data from external sensors (e.g., pressure sensor) • Flexible VLOGIC reference voltage supports multiple I2C interface voltages • 1024 byte FIFO buffer reduces power consumption by allowing host processor to read the data in bursts and then go into a low-power mode as the MPU collects more data • Digital-output temperature sensor • User-programmable digital filters for gyroscope, accelerometer, and temp sensor • 10,000 g shock tolerant • 400 kHz Fast Mode I2C for communicating with all registers • MEMS structure hermetically sealed and bonded at wafer level, and more.

For motion processing • Internal Digital Motion Processing™ (DMP™) engine supports 3D MotionProcessing and gesture recognition algorithms • The MPU-9150 collects gyroscope, accelerometer and magnetometer data while synchronizing data sampling at a user defined rate. The total dataset obtained by the MPU-9150 includes 3-Axis gyroscope data, 3-Axis accelerometer data, 3-Axis magnetometer data, and temperature data. • The FIFO buffers the complete data set, reducing timing requirements on the system processor by allowing the processor burst read the FIFO data. After burst reading the FIFO data, the system processor can save power by entering a low-power sleep mode while the MPU collects more data. • Programmable interrupt supports features such as gesture recognition, panning, zooming, scrolling, zero-motion detection, tap detection, and shake detection • Digitally-programmable low-pass filters. • Low-power pedometer functionality allows the host processor to sleep while the DMP maintains the step count. The SiP further includes on-chip timing generator ±1% frequency variation over full temperature range and optional external clock inputs of 32.768 kHz or 19.2 MHz.

Module 120 may further include a barometric pressure sensor MS5611-01BA. The MS5611-01BA consists of a piezo-resistive sensor and a sensor interface IC. The main function of the MS5611-01BA is to convert the uncompensated analogue output voltage from the piezo-resistive pressure sensor to a 24-bit digital value, as well as providing a 24-bit digital value for the temperature of the sensor. It is made clear that use of a pressure sensor is merely exemplary and may or may not be included in other embodiments of the innovative module. Even with relation to the embodiment illustrated in the Figure it is made clear that the barometric pressure sensor is optional and not necessarily considered integral to functioning of the module.

For communications, the module includes a wireless transceiver. Wireless transceiver is optional and the communication can be performed by other wired and/or other methods. Exemplarily, the transceiver is a BLE transceiver. In the exemplary depicted embodiment, the module 120 includes a CC2640 Bluetooth Smart Wireless MCU made by Texas Instruments headquartered in Dallas, Tex., USA. The CC2640 contains a 32-bit ARM Cortex-M3 processor running at 48 MHz as the main processor and a rich peripheral feature set, including a unique ultra-low-power sensor controller, ideal for interfacing external sensors and/or collecting analog and digital data autonomously while the rest of the system is in sleep mode.

It is made clear that any comparable wireless technology capable of effecting the functions described herein are considered to be within the scope of the invention. Alternatively, there may be no wireless module included in unit. The foregoing description is merely exemplary and in no way intended to limit the scope of the invention described herein. As discussed elsewhere herein, in some embodiments, more than one module 120 is placed on a player. In such embodiments, the wireless transceiver facilitates communication between the various modules on the player. Additionally or alternatively, the wireless transceiver communicates data from the module or modules to the data gateway (housed in the synchronizing station 14) and/or to a central hub and/or directly to the servers 16.

Module 120 further includes a microcontroller which is adapted to control processing functions of the module. In the depicted schematic, there is provided an embedded microcontroller STM32F411CEY6TR for an integrated circuit (IC) which is manufactured by STMicroelectronics headquartered in Geneva, Switzerland. Once again it is made clear that the aforementioned microcontroller is merely exemplary and any microcontroller, processor, processing unit, CPU or comparable component can be substituted for the aforementioned embedded microcontroller, and are therefore included within the scope of the invention.

Module 120 further has a power source. Preferably the power source is a rechargeable battery. However, any type of relevant power source can be used. In the depicted module in FIG. 2, the power source is a 3.7V lithium-ion polymer battery (Li—Po). Of course, as mentioned, the use of a Li—Po rechargeable battery is merely exemplary and not intended to be limiting in any way. In some embodiments, module 120 may further include one or more of: a physiological sensor or set of physiological sensors; a memory; a processor; a mounting mechanism; a tether; a strain gauge; and a waterproof casing.

A single module 120 may be configured to function independently, or a group of modules 120 may be configured to function in an integrated fashion. For example, an exemplary configuration includes three wirelessly integrated modules, worn on different places of the body, e.g. a module is mounted on each piece of footwear and the third module is mounted on somewhere on the upper body of the player.

The data from the modules is optionally transmitted between modules using a local wireless protocol, e.g. Bluetooth Low Energy (BLE). Multiple modules on a located on a single individual can form a WPAN. A wireless personal area network (WPAN) is a low-powered PAN carried over a short-distance wireless network technology such as, but not limited to: INSTEON, IrDA, Wireless USB, Bluetooth, Z-Wave, ZigBee, etc.

In some configurations, one of the modules can act as a local hub. Each module can calculate its own data or the hub can receive raw data from each of the modules and then integrate and calculate derived quantities from the data from all three modules. One or more modules may function independently of the central hub.

Some embodiments may not include a central hub. In some embodiments, the local hub or one or all modules may communicate the data (raw or calculated) and improvement strategy to another user or an external display or calculation units. Additionally, or alternatively, data may be sent for remote coaching and/or monitoring of a sporting event and/or for broadcast, for example via display on an electronic billboard to sports fans or via radio, TV and/or the Internet. In such cases, the data, whether raw or calculated, may be streamed in real-time from modules to a central hub or gateway or the like. If the data is raw data, then the calculations may be done at the hub or gateway or a local computing unit. Alternatively or additionally, the data may be uploaded to the server(s) for processes and returned to the gateway computer and displayed on the GUI, e.g. in the form of a dashboard.

The terms "local hub", "central hub", "gateway", "local computing unit" and "external computing device" are used herein interchangeably and can refer to a footwear sensor unit, the synchronization station, an unnamed local computer, the server computer or some or all of the above. As such, for example, communication between a footwear sensor unit and a local hub refers equally to communication between the footwear sensor unit and another footwear sensor unit, an unnamed computing device (e.g. a laptop, smartwatch etc.), the data gateway synchronization station and/or the computer server.

Footwear Sensor Mounting System

Figure 3A:
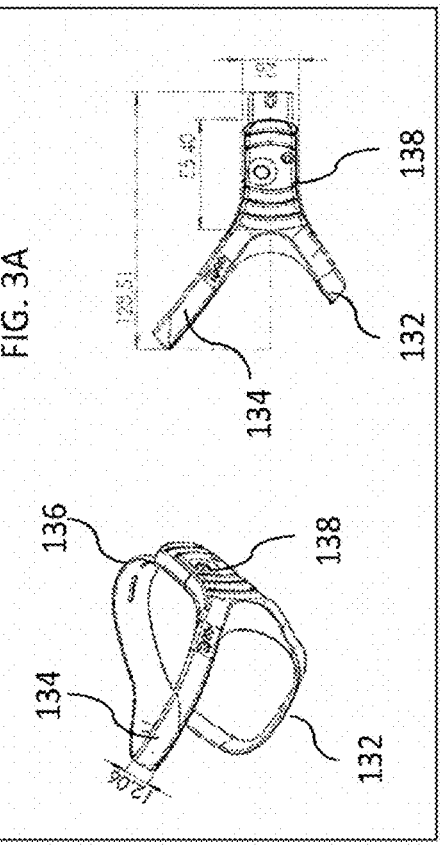
FIG. 3A is an exemplary mounting strap 130 of the mounting system.
Figure 3:
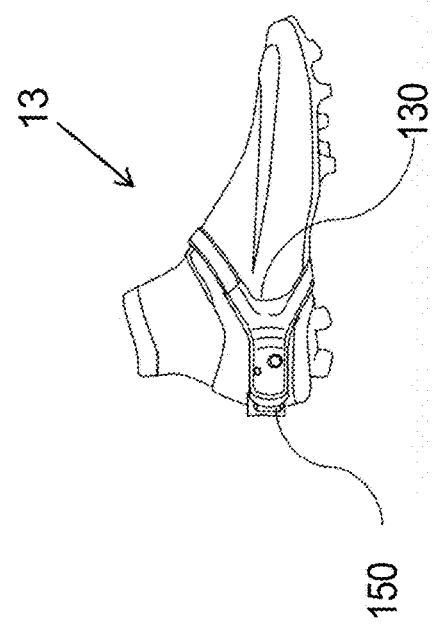
FIG. 3 is a footwear sensor unit 12 mounted on a soccer boot.

FIG. 3 depicts a footwear sensor unit 12 mounted on a soccer boot. The footwear sensor unit 12 includes the motion sensor module, the house and the mounting strap. The housing and mounting strap are alternatively referred to herein as the mounting system (or variations thereof. As mentioned, the mounting system consists of two components: a plastic housing and a flexible and/or elastic strap. The plastic housing encases the motion sensor (such as module 120 described above). The housing is inserted into a compartment on the elastic strap. The strap is mounted on the soccer boot (also referred to herein as cleats, soccer cleats, studs, soccer shoes). FIG. 3 depicts a soccer boot (which is merely a workpiece in this case) with the elastic strap mounted thereon. The strap may alternatively be made from any resilient, flexible and elastic material that can be stretched and flexed into place on the boot and withstand the rigors of running, kicking a ball and contact with other players, while remaining securely in place and not snapping.

The footwear mounting system 13 refers to the footwear sensor unit 12 but without the motion sensor package. The mounting system 13 is designed to endure the harsh environment of a football match or training session. Both the strap 130 and the housing 150 are made from rugged, heavy-duty material that is needed to withstand the constant rubbing against the ground (under-strap) and numerous impacts from the soccer ball and other objects such as other players' feet.

The sensor board (e.g. a printed circuit board with components such as or similar to those disclosed above with reference to FIG. 2) is hard mounted in the plastic housing which is designed to keep the PCB safe from any impact it might endure during a football match or training session.

Furthermore, the unique design of the strap places the housing in a "ball-free shoe zone", where the ball is least likely to hit the housing. The placing of the housing (casing for the motion sensor) is important for two reasons, (1) so that the housing does not interfere with the way the ball is kicked; and (2) to prevent damage to the unit. Moreover, the strap is designed in such a manner that all foot movement is directly transferred to the motion sensor as if the foot and the sensor unit formed a single, rigid body.

FIG. 3A illustrates an exemplary mounting strap 130 of the mounting system 13. The mounting strap is preferably formed as a single piece of material that includes a back-strap 136, an upper-strap 134 and an under-strap 132. The back-strap 136 is U-shaped where the open ends of the U split into the upper-strap and under-strap, both of which make closed circuits of their own. The back-strap is adapted to be fitted around the heel of a soccer boot while the front on the soccer boot slips between the upper-strap and the lower strap. The upper-strap 134 is adapted to lie across the top rim (or near the top rim) of the upper of the boot (the upper is the entire part of the shoe that covers the foot) and to cover over the shoelaces near the tongue of the boot. The under-strap 132 is adapted to be fitted under the bottom of the boot and to traverse the sole of the boot across an area of the sole which is devoid of cleats (studs). The design, flexibility and elasticity of the mounting strap ensure that the strap in held tightly in place, without shifting position. In embodiments, the strap is adjustable and may or may not form a closed circuit, i.e. two end of the strap may be open. In other embodiments, the strap is not adjustable. Straps come in different sizes and can be matched to the given shoe size. The straps can include some or all of the elements described above.

Both right and left-hand mounting straps are provided. For a right boot, the mounting strap includes a holding pouch 138 on the right-hand prong of the U of the back-strap 136 as viewed from behind the strap and above. For a left foot boot, the holding pouch 138 is located on the left prong of the U when viewed as above.

When mounted on a soccer boot, the holding pouch 138 is positioned on the outside of the foot/boot at the heel, below the ankle joint. This area of the boot is considered the "ball-free shoe zone" as almost no contact with the ball (except for incidental contact or specialized movements) is expected. Most contact with the ball is either at the inner side of the foot/boot or over the entire area of the foot in front of the leg. The pouch 138 is preferably positioned in line with and/or slightly behind the ankle joint.

Figure 3B:
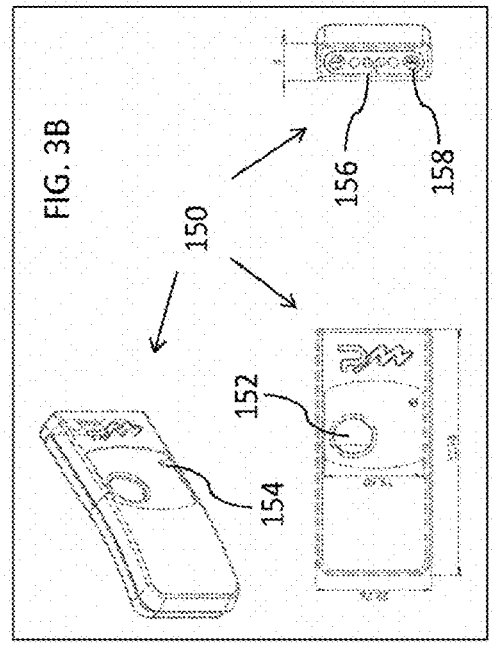
FIG. 3B is an exemplary housing or casing 150 for the motion sensor.

FIG. 3B illustrates an exemplary housing or casing 150 for the motion sensor. The housing 150 is removably insertable into pouch 138 of the mounting strap 130. In the exemplary, depicted embodiment, the housing includes a button aperture 152 via which an operator can actuate the button that activates the motion sensor unit. The casing further has an opening 154 through which an LED indicator light or lights can be seen. The lights indicate the status of the motion sensor unit. Various potential states of the motion sensor unit include active (i.e. sensing and recording), idle, transmitting, charging, low battery, etc. Other embodiments of the housing may or may not include the same or similar apertures and may or may not have alternative or additional apertures and/or structural elements.

In the depicted embodiment, the housing further includes power contacts/ports and/or data ports. For example, ports 158 may be power ports for charging the rechargeable battery of the sensor unit (e.g. module 120) and contacts 156 may be data ports for transferring stored sensor data (raw or calculated) via a physical medium. Alternatively, the ports 158 may be for data transfer while the contacts 156 may be for charging the unit. In other embodiments, apertures 158 may be for simply securing the housing in place while the battery draws charge via contacts 156. The foregoing configurations are merely exemplary and it is made clear that any configuration for charging and/or transferring data is included within the scope of the invention.

Figure 8A:
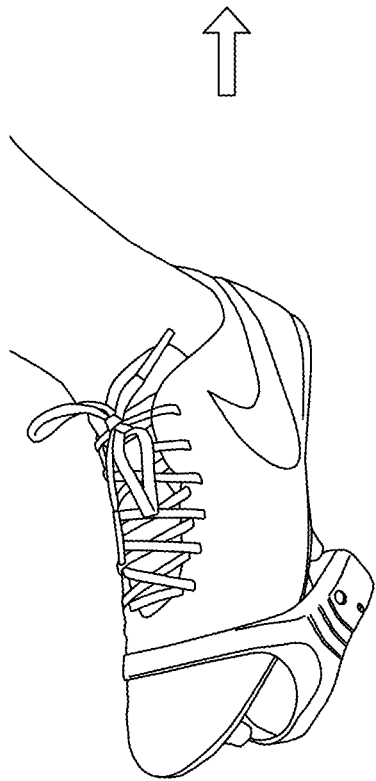
FIG. 8A-8D are illustrations depicting how the mounting system is mounted onto a soccer boot.
Figure 8B:
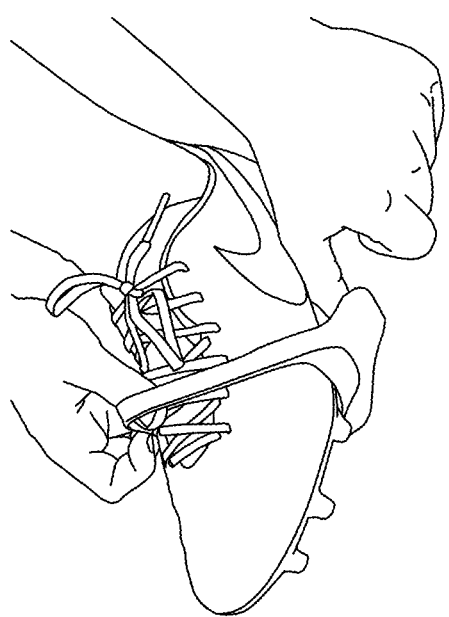
Figure 8C:
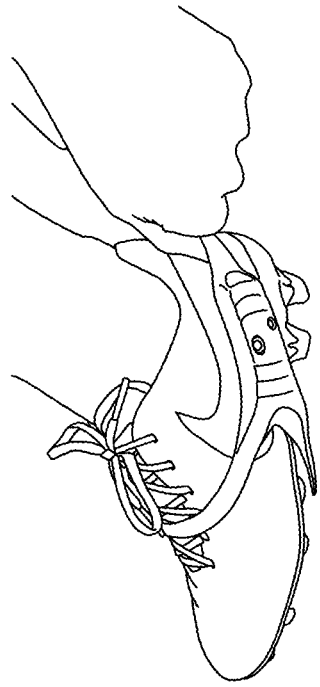
Figure 8D:
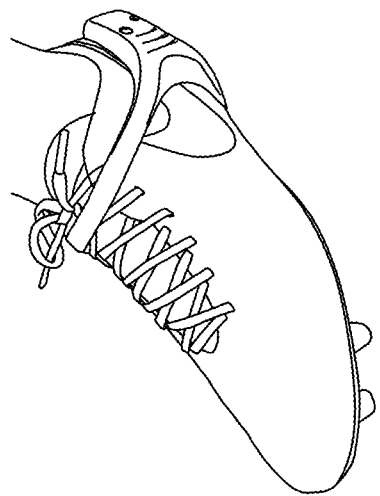

FIGS. 8A to 8D illustrate how the mounting system is mounted onto a soccer boot. FIG. 8A illustrates the initial step of strapping the mounting strap. The tip of the soccer boot is threaded over the back-strap and the under-strap, with only the upper-strap going over the top of the boot. FIG. 8B illustrates how the mounting strap is pulled in the direction of the heel, until the upper-strap is tight against the top of the boot. As depicted, it is helpful to slide one thumb under the upper-strap, to position the upper-strap as close to the tongue as is comfortable and/or as the elasticity of the strap allows. The second thumb can be used to hook the back-strap and draw it behind the heel of the boot, as is shown in FIG. 8C. Depending on how taut the strap is, it may be necessary (or at least helpful) to use the first hand as well (as depicted). Finally, the mounting system with the motion sensor unit is properly mounted on the boot and positioned optimally, as discussed above.

The core technology of the innovative system 10 is buried within a unique, dedicated algorithm designed and configured to solve different classifying, estimation and data fusion problems. The system algorithm is based on three key components: (1) Footwear Event Detection; (2) Football Gait Tracking; and (3) Football Sensor Data Fusion.

Footwear Event Detection

The foot-based activity and event detection algorithm provides the ability to detect different footwear movements and ball interaction events (such as, for example, ball touch, full instep kick, ball receive, ball release, cross-over, etc., referred to herein as 'classes') using a single 6 DOF motion sensor (3-axis accelerometer, 3-axis gyro). The classifying problem is very complex due to the large variance of movement between different players (different ages, different playing technique, etc.), the similarity between the movement of the different classes and the similarity between any football movement and the different classes.

In order to solve the aforementioned classifying problem, a machine learning method has been employed. The first step in the machine learning approach is to gather and label a large data set of the relevant movement type. For the instant system, the data set was collected from different types of football clubs at regular training sessions and during matches.

In order to label the data, recorded motion data and corresponding video data were sourced. The two data sources were synchronized and the resulting output was set as an input to a unique tagging system developed for the purpose of classifying the data. Once the large data set had been gathered, the relevant features were extracted from the raw data and run as a machine learning training process. Understanding the physics of the foot-based events allows operators to extract special motion features that can be used to feed different machine learning algorithms and thereby achieve a high success rate of event detection. For example, the maximum foot height (at the end of back swing and end of front swing) is classified as a kick event feature.

Figure 4:
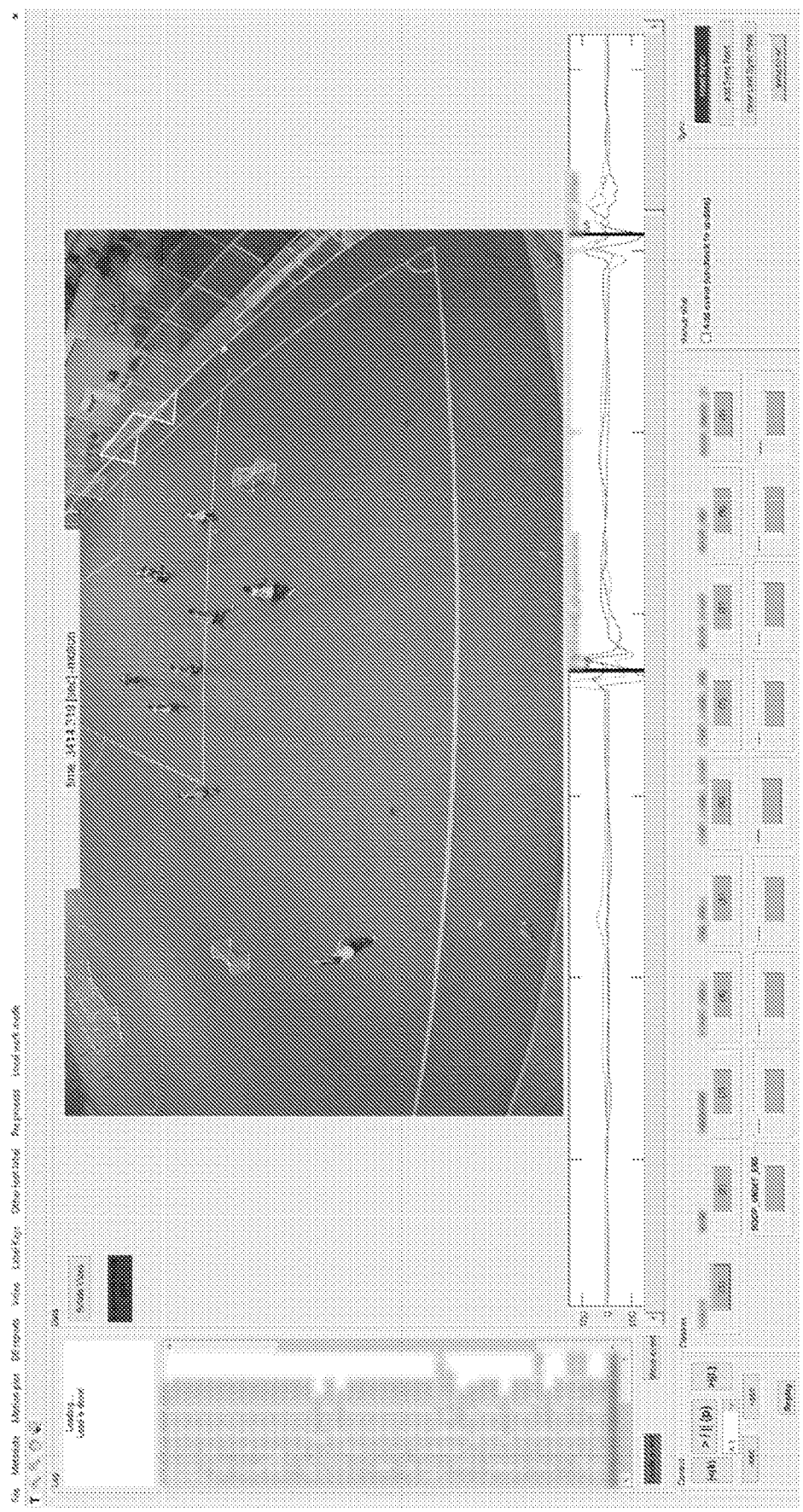
FIGS. 4 and 4A are screenshots of the innovative labeling software where video data is synchronized with motion data.
Figure 4A:
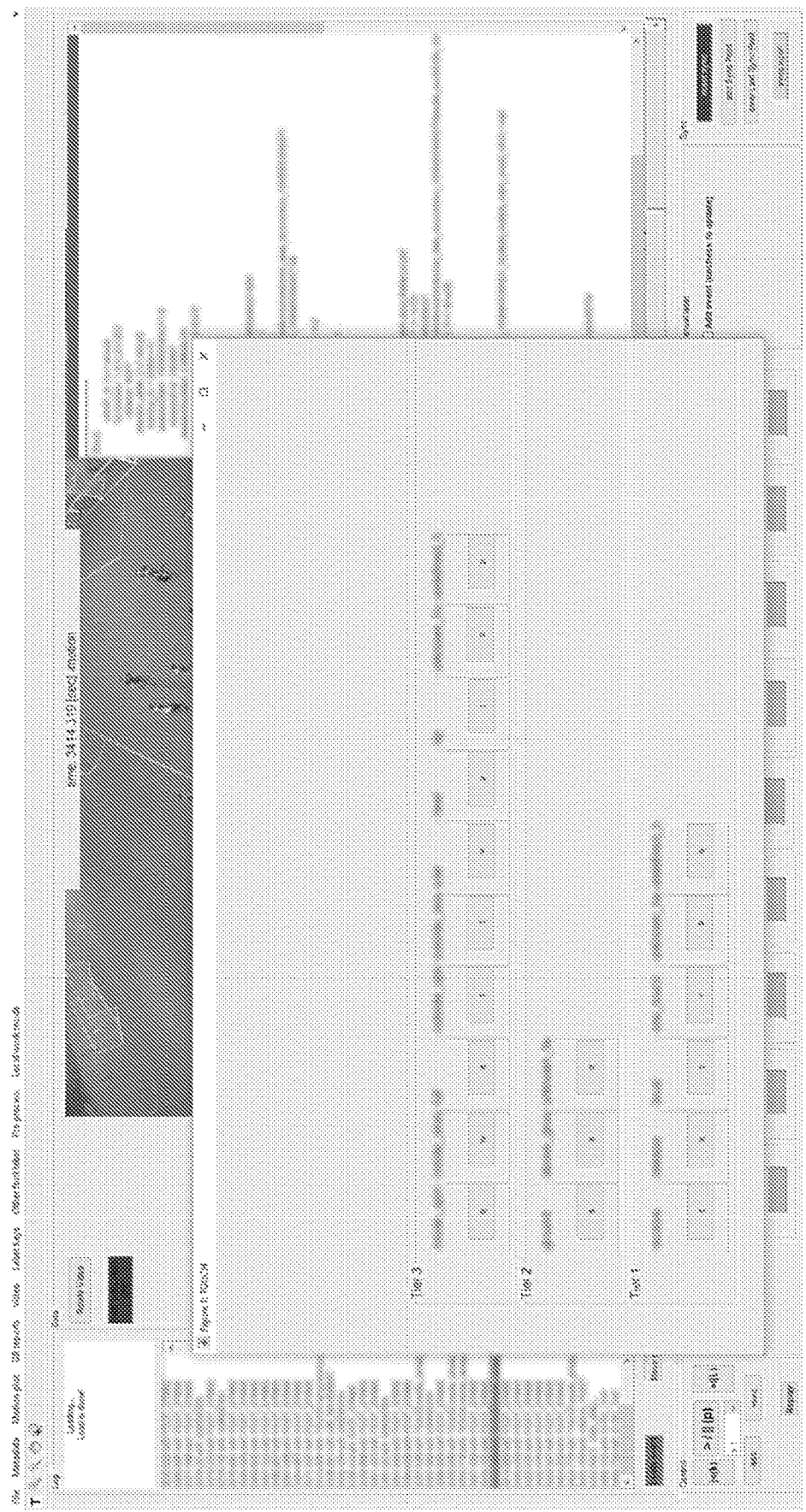

FIG. 4 is a screenshot of the exemplary innovative labeling software where video data is synchronized with motion data. On the left side of the screen is an event list of all commonly found events. The operator can choose from the events list and watch about a second of video around the event so that the event can be correctly labeled. On the bottom part of the screen are label buttons. Some buttons open a sub menu which provides further labeling options. FIG. 4A is a screenshot similar to FIG. 4, but with a sub-menu open. The operator can also watch the video freely and add events to each player on the screen. The plot below the video is the acceleration data, as it was recorded by the sensors, this data helps the operator to accurately add an event.

Football Gait Tracking

The goal of the gait tracking algorithm (GT) is to track the orientation and translation of the player during the gait cycle (walk/run cycle) and extract physical parameters (exemplary extracted parameters are discussed below with relation to Table 1). In recent years, work has been done in the field of inertial sensor gait tracking and various articles have been published. In addition, inertial sensor-foot mounted GT projects were conducted in a few universities, in an attempt to solve problems relating to rehabilitation and indoor navigation. However, none of the aforementioned attempts has provided a solution that is robust enough to handle the complex movements that occur in a football match or training session. Based on prior work in the field, the translation calculation can, theoretically, be solved with double integration of the local frame acceleration profile:

$$\vec{p}_L = \iint \vec{a}_L dt \quad \text{Equation 1}$$

$$\vec{a}_L = R_L^S \otimes \vec{a}_s \quad \text{Equation 2}$$

Where $\vec{p}_L$ is the position of the sensor on the local frame, $\vec{a}_L$ is the acceleration on the local frame, $R_L^S$ is the rotation matrix from the sensor frame to the local frame (the sensor orientation) and $\vec{a}_s$ is the raw acceleration on the sensor frame (sensor output). However, with the double integration method calculation and measurement errors accumulate over time and since the acceleration is measured under a finite rate it also means that some of the acceleration data is missed, resulting in a growing error in the translation calculation.

To solve the drift problem, additional information is needed regarding the gait that will allow for calibration of the sensor measurement error and will limit the problem under a finite error. The zero-velocity update (ZUPT) is a well-known concept for this purpose, and a detection of the zero-velocity state of the foot can contribute to state vector, for example, when using a Kalman Filter estimator.

A single gait cycle is also known as a stride. Each gait cycle or stride has two phases: Stance Phase, the phase during which the foot remains in contact with the ground, and the Swing Phase, the phase during which the foot is not in contact with the ground. The mere detection of ZUPT in a gait cycle is not sufficient when performing complex gait movements like in a football game (kicking, tackling, cross-overs, etc.) and shows low performance of step length and velocity. In-order to deal with those complex gait types there is presently described herein an advanced gait phase detection (GPD) for football movement using state of the art machine learning algorithms based on a large data set gleaned from multiple football training sessions and matches. The advanced gait phase detection process detects the zero velocity phases more efficiently and, in addition, detects zero height phases (ZHUPT) which usually occurs during the stance phase. The aforementioned detections are used as input to the Kalman Filter and affect the position and velocity estimation.

The development of gait phase detection (GPD) required a large, labeled data set, of various types of football movements. The labeled data set was created using the labeling system as discussed above. A ML based classifier was designed that classified events in the large data set under the classes: (1) heel-strike (2) toe-off (3) zero-velocity (4) none-gait movement.

Figure 5:
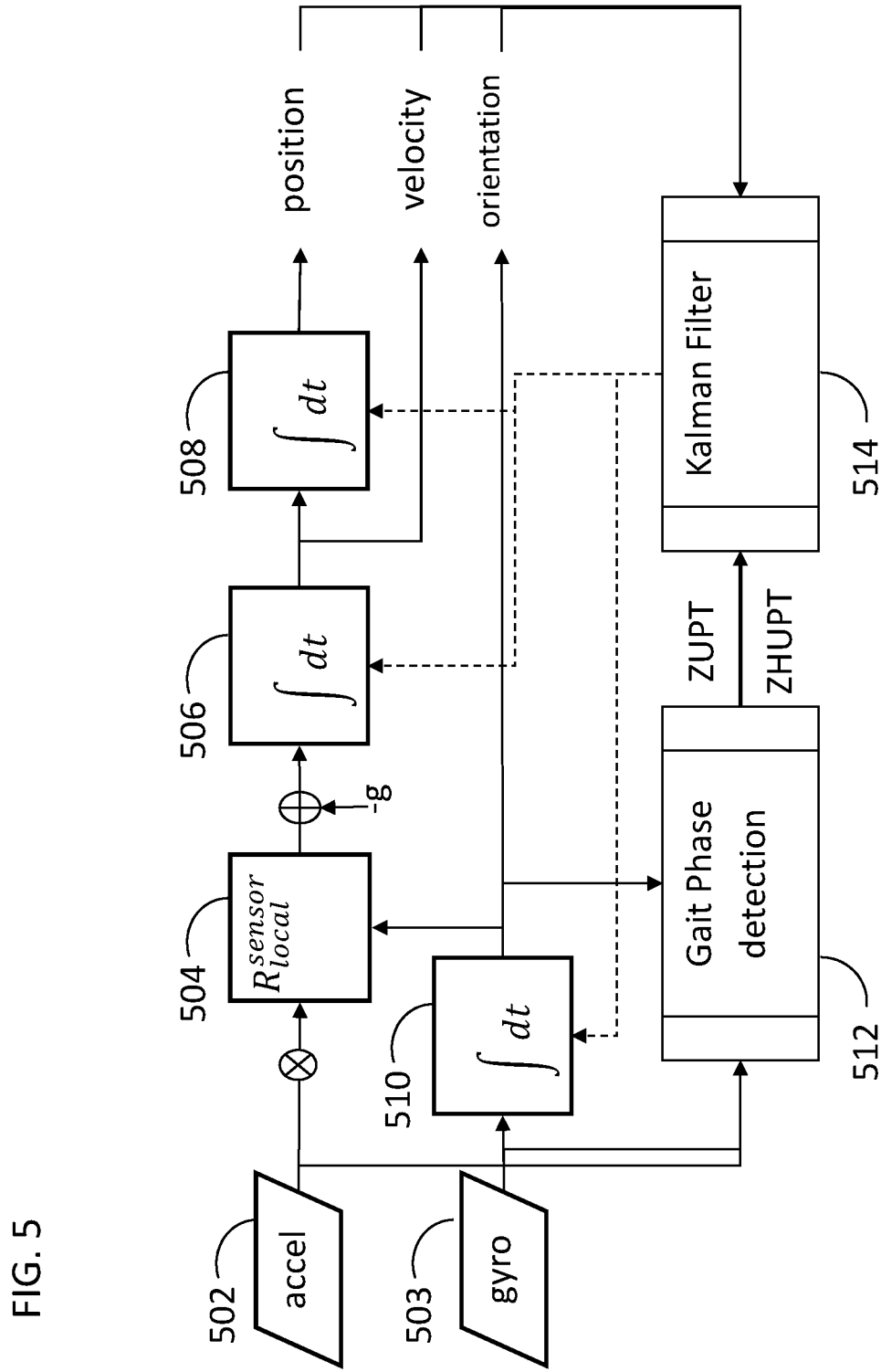
FIG. 5 is a flow diagram of the rotation matrix that transforms the accelerations from the sensor frame to the local frame.

FIG. 5 illustrates a flow diagram of the rotation matrix that transforms the accelerations from the sensor frame to the local frame. In the diagram, $-R^{foot}_{local}$ is the rotation matrix, the "+" sign indicates a sum, the "X" indicates a cross product and the "∫" sign indicates an integration in time.

At block 502 the processor receives sensor data from the accelerometer. At block 503 the processor receives the sensor data from the gyroscope. At block 504 the acceleration data rotated to the local frame and then subtracted by g on the local z-axis. At block 506 the processed acceleration data is integrated and the velocity vector is formed at block 508. The velocity is integrated and the position vector, along with the velocity vector, is used at block 514, with the Kalman Filter. At block 510 the gyro data is integrated for calculation of $R_L^S$ (that is used in block 504) and for the detection of ZUPT and stance, along with the raw acceleration and gyro data, at block 512.

Figure 6:
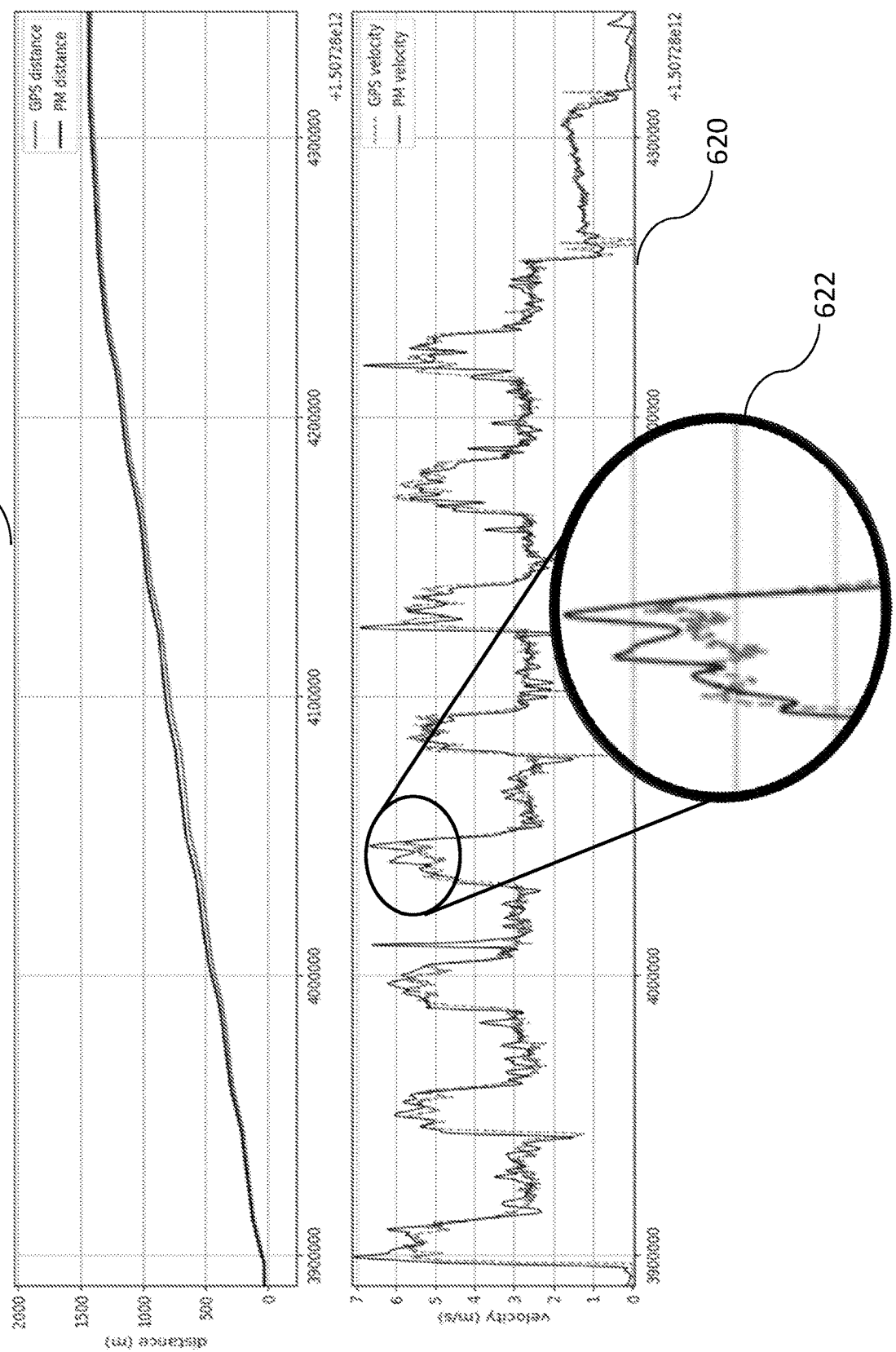
FIG. 6 is a depiction of two graphs comparing the innovative system with a legacy GPS based system.

FIG. 6 includes two graphs comparing the innovative system with a legacy GPS based system. In the top graph 610, the detected distance from a GPS based system ("GPS distance") is compared to the detected distance of the footwear sensor unit ("PM distance"). In the bottom graph 620, the velocity detected by the two devices is compared. The velocity of the players detected by the GPS based system ("GPS velocity") is denoted with a broken line and the velocity detected by the innovative footwear sensor unit ("PM velocity") is denoted by a solid line. A magnified portion 602 of the graph shows an exemplary peak where the footwear sensor unit detects the high velocity of the player with greater precision than the GPS bra.

Football Sensor Data Fusion

The present innovative system gathers information from multiple sensors with theoretically no upper limit of sensors. For example, a two-team match provides data from 42 sensors (22 player each having two sensors). The presently disclosed sensor data fusion process utilizes the extra information gleaned from having the entire team sensor data provided in parallel. For example, during a football game only one player can have possession over the ball at a given time since there is only one ball in the field.

The sensor data fusion takes inputs such as the individual positions of the players, the velocity of each of the players, the number of touches, possession time, etc. Based on the sensor data, the system defines the individual ball possession (which player was in possession of the ball and for how long, etc.), eliminates false ball touch detections and defines accurate and inaccurate passes. Furthermore, the system uses the types of ball touches and other parameters to find the most likely sequence of hidden states or a "Viterbi Path" that optimizes different probability matrixes built with the machine learning process. Eventually, the sensor data fusion outputs parameters including: updates for the classifier results, estimation of individual ball possession, estimation of team ball possession and more.

Figure 7:
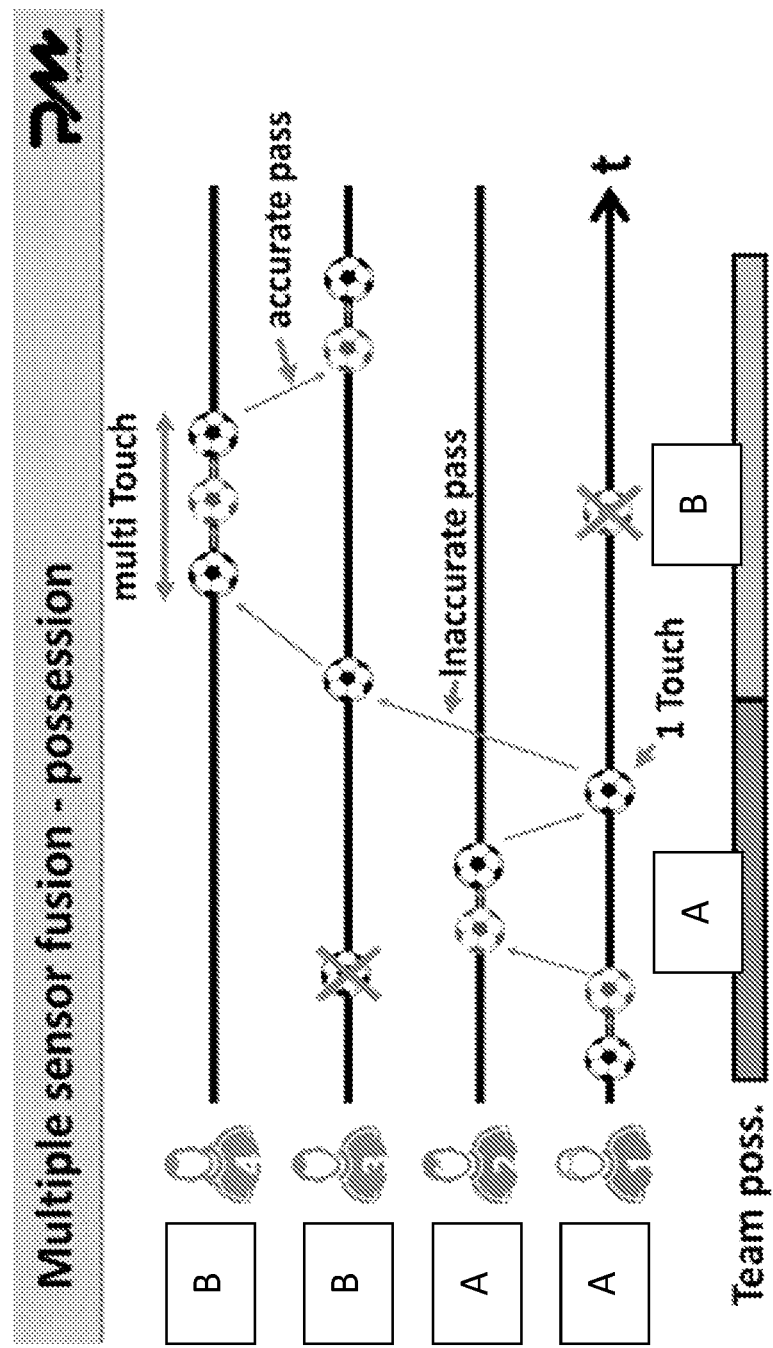
FIG. 7 is an illustrative depiction of sensor data that is fused to present a timeline that is congruent with the actual play.

FIG. 7 is an illustrative depiction of sensor data that is fused to present a timeline that is congruent with the actual play. In the Figure, players 1 and 2 are on team A and players 3 and 4 are on team B. As the timeline progresses from left to right, various events are detected. At first, player 1 is in possession of the ball and at the next detected event, the ball is touched by player 2. Between the two events a false ball-touch-event detection is eliminated.

At the next point in the timeline the ball is once again touched by player 1 who makes an inaccurate pass to player 3 from the opposing team (team B). The algorithm deems this pass as inaccurate because the ball was not passed to a team member but rather the ball was intercepted by player 3. Furthermore, the inaccurate pass was performed by a single touch by player 1. Exemplarily, a coach can analyze what went wrong with the single-touch pass and how to improve the player's technique.

Looking back at the timeline, player 3 passes the ball to player 4 who dribbles the ball (deduced by the multiple ball-touch detections). At the same time, another ball-touch for player 1 is detected. The algorithm determines that the ball touch is false and therefore eliminates the event. A ball touch is next detected at player 3. The system determines that the ball was passed by player 4 (who previously has multiple ball touch events) to player 3. The system also concludes that the pass was an accurate pass as player 4 and player 3 are both on team B.

Extracted Parameters

The smart footwear of the immediate invention is focused on improving technical and tactical performance of individual soccer players as well as entire teams by extracting performance statistics of the players on an individual level as well as on a group level. The innovative system is based on three main elements: (1) tracking players' movements on the field; (2) detecting ball touch events and recognizing the different types of ball-touch events; and (3) performing data fusion from sensors located on multiple players. Various parameters are extracted from training sessions and matches using the aforementioned three elements. FIG. 9 includes Table 1 which details examples of how the above described components of the system are employed to extract various parameters.

For example, on the topic of touch count, when a sensor detects that a ball-touch event has occurred, there are various pieces of information that can be learned from the statistical data. The touch count can quantify the player involvement from a coaching and performance point of view. Further, the touch count can quantify the control the player has in both legs. Also, the data can be used to identify weaknesses in the player's ball control. The parameters that can be extracted from the sensor data include, but are not limited to: a total touch count, leg use and touch type distribution. The total touch count is the sum total of all ball touches of a single player in a training session and/or a drill. Leg use refers to the statistic of the ball touch count for each leg divided but the total touch count. Touch type distribution refers to the sum total of ball touches per type (e.g. receiving, releasing, dribbling, etc.). In a similar fashion, the table details the topics of ball possession (BP), passes, retrieves, possession lost and physical characteristics of the players.

Another aspect of the innovation is relate to improving physical performance of an individual athlete. The data allows the system to provide further breakthrough features in relation to physical performance. For example, physical parameters extracted from the sensor data and/or event data can show mechanical workload of a player divided by each foot and in direct relation to the foot (rather to other locations on the athletes like hand, back etc.). Another example extracted parameters is injury prediction indication and injury prevention capabilities. The aforementioned exemplary parameters are extracted from the data by gathering information which is related to unique bio-mechanical features of the athlete motion.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A system for extracting performance parameters from at least one footwear sensor unit, the system comprising the at least one footwear sensor unit and at least one mounting strap,
   wherein each of the at least one footwear sensor unit comprises:
   an Inertial Measurement Unit (IMU) including a 3-axis accelerometer and a 3-axis gyroscope, said IMU adapted to gather sensor data of detected movements of the footwear,
   a storage device in electronic communication with said IMU, said storage device for storing said sensor data;
   a communications module in electronic communication with said storage device, said communication module configured to transmit data to an external computing device; and
   a processing unit in electronic communication with said IMU, said processing unit:
   receiving, at a processing unit, sensor data from said IMU; and
   classifying a set of said sensor data as event data indicative of a gait event, and
   wherein the at least one footwear sensor unit is inserted in said mounting strap, said mounting strap adapted to be fitted onto the footwear and the at least one footwear sensor unit is positioned at an outside ankle area of the footwear,
   wherein said classifying of said event data indicative of said gait event is performed by applying a machine learning (ML) based classifier to detecting zero velocity phases and zero height phases, the detected zero velocity phases and zero height phases input to a Kalman filter to affect an estimation of position and velocity, and
   wherein the ML based classifier is trained on a data set with each event labeled as either a heel-strike event, a toe-off event, a zero-velocity event and a none-gait movement event.

2. The system of claim 1, wherein said classifying of said event data indicative of said gait event is performed by employing a gait phase detection algorithm.

3. The system of claim 1, wherein the received sensor data comprises a plurality of sets of sensor data being indicative of gait events, foot activity events and ball touch events, and
wherein, for each of said plurality of sets of sensor data, said processing unit is configured to classify said respective set of sensor data as being indicative of a gait event.

4. The system of claim 3, wherein said classifying of said event data indicative of said foot activity event or said ball touch event is performed by employing a foot-based activity and event detection algorithm.

5. The system of claim 3, wherein said performance parameters include one or more of: a Total Touch Count, Leg Use, Touch Type Distribution, ball possession (BP), Individual BP (IBP) total count, individual BP type count, BP time distribution per player and per team, Team BP (TBP) time, Total pass count per player and per team, Successful pass percentage per player and per team, a Passing network, Passes per team possession, a Retrieve count, a Retrieve effort indicative of effort made after team loss of possession, a Possession lost count, an average Retrieve time per player and per team and physical performance parameters.

6. The system of claim 5, wherein said physical performance parameters are selected from the group including: a total distance traversed per player, a distance per drill, a distance per speed zone, a maximum speed, a Work rate, a Sprint count, a Sprint distance, Acceleration and Deceleration count by zones, and a total mechanical load per player.

7. The system of claim 3, wherein said classifying comprises applying a gait tracking algorithm and a foot-based activity and event detection algorithm, said gait tracking algorithm providing an ability to track orientation and translation of the participants during a gait cycle; and said foot-based activity and event detection algorithm providing an ability to detect different footwear movements and ball interaction events.

8. The system of claim 1, wherein said applying the ML based classifier comprises:
responsive to the output of the Kalman filter estimator, integrating sensor data from the gyroscope; and
inputting the integrated sensor data from the gyroscope, the sensor data from the gyroscope and sensor data from the accelerometer into the ML based classifier.

9. The system of claim 8, wherein the estimation of the position and velocity comprises:
rotating the sensor data from the accelerometer to a local frame;
responsive to an output of the Kalman filter estimator, integrating the rotated data to form a velocity vector; and
responsive to the output of the Kalman filter estimator, integrating the velocity vector to form a position vector.

10. The system of claim 9, wherein the velocity vector, the position vector and an output of the ML based classifier are input into the Kalman filter estimator.

* * * * *